(12) United States Patent
Stephens et al.

(10) Patent No.: US 9,873,031 B2
(45) Date of Patent: Jan. 23, 2018

(54) SMART TARGET SYSTEM FOR COMBAT FITNESS AND COMPETITION TRAINING

(71) Applicant: CELLPOINT SYSTEMS, INC., San Francisco, CA (US)

(72) Inventors: Richard Stephens, San Francisco, CA (US); Jin Song, Saratoga, CA (US)

(73) Assignee: CELLPOINT SYSTEMS, INC., San Francisco, CA (US)

(*) Notice: Subject to any disclaimer, the term of this patent is extended or adjusted under 35 U.S.C. 154(b) by 0 days.

(21) Appl. No.: 13/921,141

(22) Filed: Jun. 18, 2013

(65) Prior Publication Data

US 2013/0345839 A1    Dec. 26, 2013

Related U.S. Application Data

(60) Provisional application No. 61/662,219, filed on Jun. 20, 2012.

(51) Int. Cl.

| A63F 9/00 | (2006.01) |
| A63B 71/06 | (2006.01) |
| A61B 5/00 | (2006.01) |
| A61B 5/22 | (2006.01) |
| A61B 5/11 | (2006.01) |

(52) U.S. Cl.
CPC ............. *A63B 71/06* (2013.01); *A61B 5/22* (2013.01); *A61B 5/6887* (2013.01); *A61B 5/1126* (2013.01); *A61B 2503/10* (2013.01); *A61B 2562/0219* (2013.01); *A61B 2562/046* (2013.01)

(58) Field of Classification Search
CPC ...................................................... A63B 71/06
See application file for complete search history.

(56) References Cited

U.S. PATENT DOCUMENTS

| 6,110,079 | A  * | 8/2000  | Luedke et al. ............... 482/83 |
| 6,575,879 | B1 * | 6/2003  | Harney ............... A63B 69/345 434/251 |
| 8,079,938 | B2 * | 12/2011 | Jones et al. ................... 482/8 |
| 8,337,366 | B2 * | 12/2012 | Jones et al. ................... 482/8 |
| 8,398,451 | B2 * | 3/2013  | Wolfe et al. ............... 446/175 |
| 8,435,121 | B1 * | 5/2013  | Fisher ................... A63F 13/12 463/16 |

(Continued)

FOREIGN PATENT DOCUMENTS

CN          202366428 U      8/2012

*Primary Examiner* — Seng H Lim
(74) *Attorney, Agent, or Firm* — Perkins Coie LLP

(57) ABSTRACT

A combat training system for competition and impact fitness training provides a feedback mechanism that supports virtual sparring. The system is designed for athletic training and game-play, for one or multiple users. Sensors attached to a target structure may capture data about strikes on the target including proximity to a target, force of impact, direction, and reaction time. A target structure may be an instrumented punching bag, mannequin, or other structure that may move when struck. Data collected by the sensors may be sent to an analytic system that updates a display presenting a cumulative score, and/or for each strike, the data collected and the points awarded. An athlete may configure the target system for a particular session such as which targets in the system are active, a point value associated with each target, and/or the force of a strike required to count as a valid strike.

32 Claims, 6 Drawing Sheets

(56) References Cited

U.S. PATENT DOCUMENTS

| | | | |
|---|---|---|---|
| 2003/0013584 A1* | 1/2003 | Harney | A63B 22/02 482/54 |
| 2005/0153773 A1* | 7/2005 | Nguyen | G06Q 30/0207 463/25 |
| 2006/0201580 A1* | 9/2006 | Kang | 144/195.5 |
| 2007/0061107 A1 | 3/2007 | Vock et al. | |
| 2008/0051228 A1 | 2/2008 | Harmon et al. | |
| 2008/0098797 A1 | 5/2008 | Considine et al. | |
| 2008/0242509 A1* | 10/2008 | Menektchiev | A63B 21/0628 482/4 |
| 2010/0130329 A1 | 5/2010 | Sullivan et al. | |
| 2011/0111924 A1 | 5/2011 | Jones et al. | |
| 2011/0159939 A1 | 6/2011 | Lin et al. | |
| 2012/0028712 A1* | 2/2012 | Zuili | A63F 13/12 463/39 |
| 2012/0184373 A1* | 7/2012 | Kim | H04L 65/4084 463/42 |
| 2012/0253484 A1* | 10/2012 | Burich | G06F 19/3418 700/91 |
| 2013/0041590 A1* | 2/2013 | Burich | G06F 19/3418 702/19 |
| 2014/0378281 A1* | 12/2014 | Mazi | A63B 69/34 482/83 |
| 2015/0031970 A1* | 1/2015 | Lain | A61B 5/14551 600/323 |

* cited by examiner

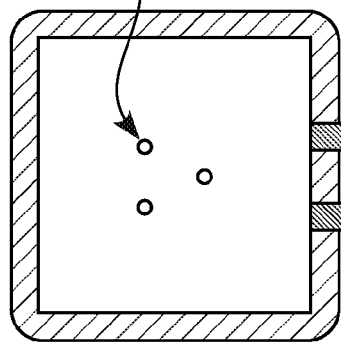
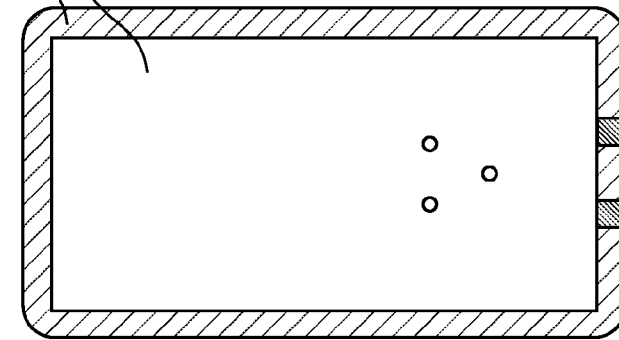
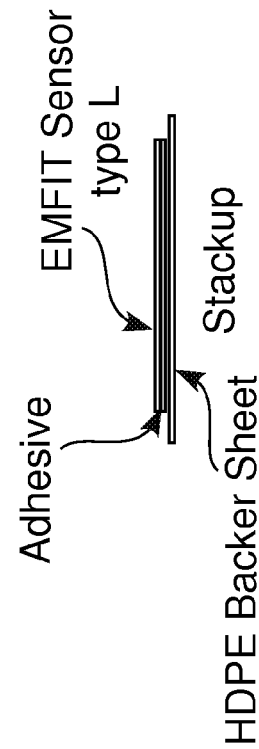
FIG. 6A
FIG. 6B
FIG. 6C

SMART TARGET SYSTEM FOR COMBAT FITNESS AND COMPETITION TRAINING

CROSS REFERENCE TO RELATED APPLICATIONS

This Application claims priority to U.S. Provisional Application No. 61/662,219, filed Jun. 20, 2012, the entirety of which is incorporated by reference herein.

FIELD OF THE INVENTION

The invention relates to using electronic sensors to evaluate and provide feedback regarding impacts during recreational activity, training, athletic competition, and electronic game play.

BACKGROUND OF THE INVENTION

In combat sports such as boxing, martial arts such as taekwondo, dueling weapons such as fencing, and so forth, athletes compete in a duel. The object is to strike blows and score points while preventing an opponent from doing the same. A strike (also referred to as an "impact") is characterized by applying force to a target with any part of the body (typically a hand, arm, foot or leg) or an inanimate object that represents a weapon. Typically, points are awarded in these competitions to athletes who successfully deliver a legal blow to designated targets. At the end of the competition, generally determined by the passage of a specific time frame, the athlete with the most points is declared the winner. Thus, training for such a combat sport requires feedback on the accuracy of a strike delivered to the designated targets, the force of the strike, the direction of the strike, and the reaction time. Athletes can improve their skill by receiving immediate and objective feedback of their performance.

Sports like martial arts, fitness and athletic training, and recreational activities have utilized targets and striking surfaces to provide focus and feedback. For example, foil fencing has long used electronic scoring that determines when a legal touch is made. In the Olympic Games of 2012, an impact measuring system was used to score TaeKwonDo competition successfully.

Related U.S. Pat. No. 7,891,231, which is incorporated herein in its entirety by this reference thereto, discloses installing an array of piezoelectric wires and magnetic field detection sensors in garments worn by an athlete to accurately evaluate and score strikes delivered in martial arts. For example, protective padding in a vest-like garment may contain sensors for detecting receipt of a strike. Boots and gloves may have embedded magnets that trigger sensors in the protective gear such as chest and head protection to detect delivery of a punch or kick. U.S. Pat. No. 7,891,231 discloses a multiple sensing algorithm to determine the efficiency of target impact. The algorithm relies on measurements from multiple different types of sensors. The force sensor, based on piezo film or piezo cable, indicates how hard the target was hit, and the magnetic proximity sensor indicates that the strike is in a appropriate target area.

The field of avionics has used IM sensors to measure aircraft motion to assist navigation. The detected motion involves roll, pitch and yaw. An IM sensor unit (IMU) typically consists of 3 axis accelerometers and 3 axis angular rate sensors to measure roll and pitch movement. In avionics, additional 3 axis magnetometers are used to measure yaw relative to earth magnetic field.

With the advent of advanced sensor technologies, new methods of impact evaluation are now possible.

SUMMARY OF THE INVENTION

A combat training system is described herein for competition and impact fitness training with a feedback mechanism that supports virtual sparring. The system is designed for both athletic training and game-play, for one or multiple users. A single user initiates a "session" by either logging into the user's account or activating the control box and sensors associated with a target system, such as an instrumented punching bag, weapon, or fixed targets attached to a wall or supporting structure. A session can be a training session, a game, or a competition. Once the session is initiated, the user may select options that specify: the number of training rounds, the length of the training round (measured either by time or the number of impacts), the interval and pattern of the impact challenges, and for playing various games against other players either locally or over a network, such as the internet.

According to an embodiment of the invention, once a session is initiated, one of the targets may flash, signaling the athlete to strike the target within a defined period of time. If the athlete successfully strikes the target within that time period, the score is recorded in the target system. The acquired data may be stored on a local device or sent to an analytic system that performs data processing and recording, which may be internet based. Subsequently, the next target in the sequence is lighted. If the athlete fails to strike the target within the measured proximity to the target or within the 'time-out' period, a null score may be recorded, and the system may continue to light the next target in the game sequence. Once the session sequence is complete, the athlete may continue in one of several ways: striking the target or activating the control box to restart the session, starting a different kind of session, or viewing the athlete's account page and activity history.

Each target system may comprise one or more targets, each of which provides a focal point for measuring and providing feedback on accuracy. The target system also may include a control box for receiving and interpreting sensor data that is generated by a strike, and a storage system for saving and retrieving the sensor data. Interpretation of the sensor data may include determining the reaction time, accuracy of a strike, how hard the strike was delivered, and/or the direction of the strike. The target system may also include sensory feedback, such as visual feedback (e.g. lights that illuminate and/or flash when a strike is registered), auditory feedback (e.g. music, tones, or spoken voice, any of which may vary in volume, pitch, and rhythm for communicating information), or tactile feedback, such as a vibration, burst of air, electric shock, temperature change, etc.

The system also includes an analytic system component comprising a backend computer system running an application for creating and managing user accounts, registering users, and associating user accounts with particular target systems. In addition, the analytic system provides a way to authenticate a user and to store data collected within a training session to be stored in association with the user's account. The application may also provide a configuration interface for setting options to be used in a particular session. The session options may determine when the session will end (time based or event based), and a point value assigned to particular types of strikes. For example, strikes may be characterized based on which of a plurality of targets is struck, accuracy for striking a particular target, direction and force of the strike, and response time. Thresholds may be set against which to compare sensor data to determine whether a valid strike was received and/or how many points to award the strike. The application may also be used to initiate a virtual multiple player competition or game in which players that are potentially geographically distant from each other may play, compete, or spar in real time. The analytic system may collect sensor data from each of the players/contestants and recognize which data is associated with which player.

During the session, the data collected by the sensors may be transmitted immediately to the analytic system where it is analyzed, stored, and reported visually to a web browser or other display system in the form of processed data and graphics showing the location, magnitude, and reaction time of each impact, all in near real-time. Additionally, the data may be retrieved by the user to see how past sessions compare, and how the user is progressing toward their training goals.

Multi-player sessions are also possible with players using the same target system, or using target systems in different locations. A multi-player session may require the athletes to respond to the same game challenge on distinct target systems, and then compare their score, or alternatively, by taking advantage of the multiple colored lights in each target, players sharing a target system may respond to challenges based on their target color, and then compare scores after the session. A multi-player session may also give feedback in the form of avatars that represent the players, showing how each player's body would respond to the strikes from the opposing player. Such an embodiment may be considered a game or virtual training session. In an embodiment, the target system being struck may be represented by the avatar.

BRIEF DESCRIPTION OF THE DRAWINGS

FIGS. 6A-6C illustrate designs for a piezo sheet sensor, according to an embodiment of the invention.

DETAILED DESCRIPTION

The nature, objectives, and advantages of the invention will become more apparent to those skilled in the art after considering the following detailed description in connection with the accompanying drawings.

An effective training tool for improving skill in martial arts and other combat sports may include the following features:

1. Accurate measurement of the magnitude of an impact delivered by an athlete to evaluate efficiency and effectiveness of various techniques.
2. Accurate representation of real world competitive environments. For example, points should be awarded when and only when a point would be awarded in a real world competition.
3. Quantitative measurement of accuracy, force, direction, and timing to allow the athletes to monitor and optimize techniques for scoring valid points most effectively. Regarding terminology used herein, a session using the combat scoring system may comprise a personal training session, personal game session, multi-player game session, or official competition. An athlete is one who participates in a session by striking a target. A user is one who accesses an application providing an account related to combat scoring sessions hosted by the backend analytic system. The user is typically the same person as the athlete, although the user may also be a coach, a parent, or a judge.
4. Feedback to the athlete, coach or interested parties in the form of data and/or graphical representations of the training sessions and related impact data.

Figure 1:
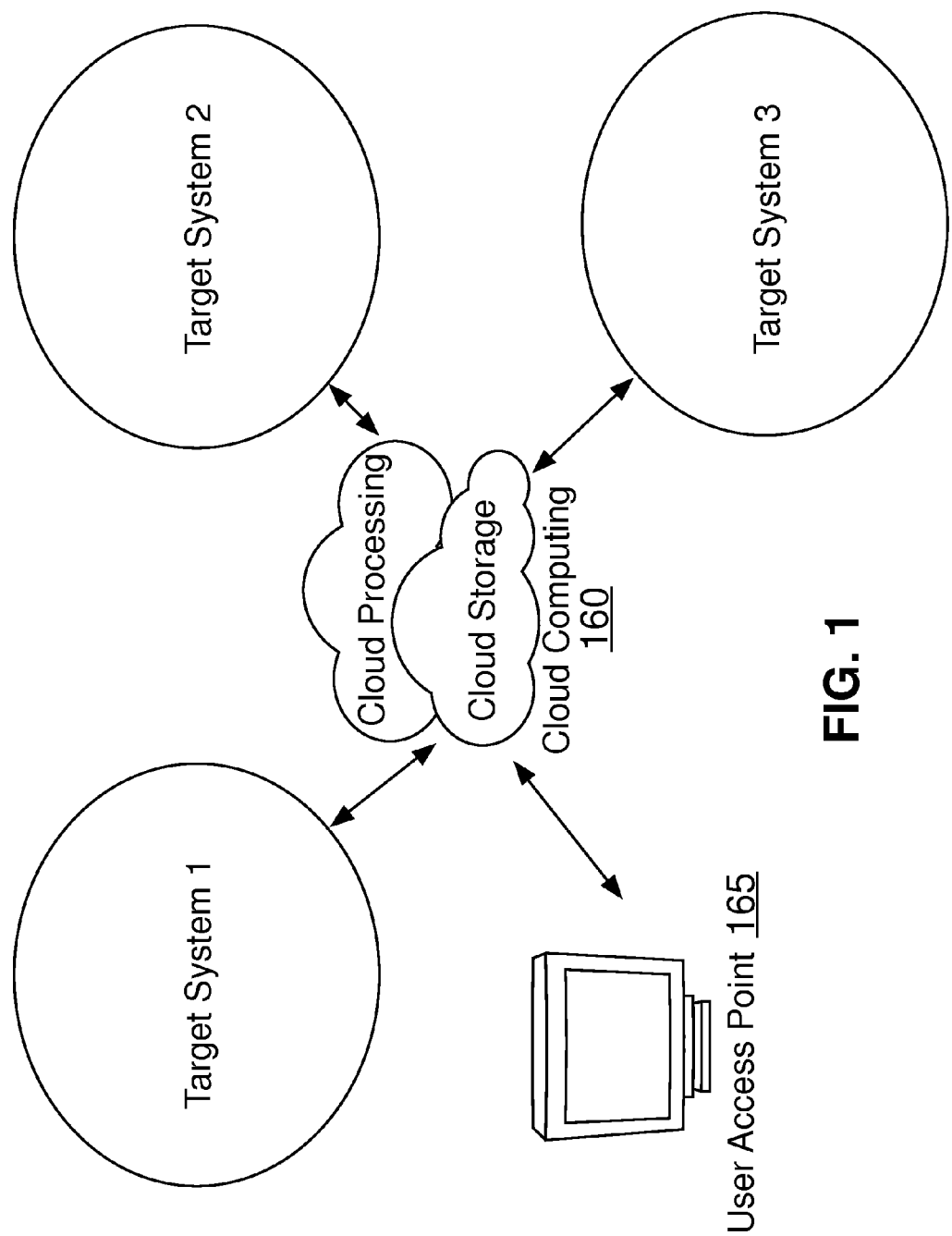
FIG. 1 is a block diagram of the components and interconnections of a combat scoring system, according to an embodiment of the invention.

FIG. 1 is a block diagram of the components and interconnections of a combat scoring system, according to an embodiment of the invention. The combat scoring system comprises one or more target systems represented by Target System 1-3 in FIG. 1. Although three systems are illustrated according to an embodiment of the invention, any number of systems may be used (i.e., three systems are neither required nor are the number of systems limited to three). According to the embodiment illustrated by FIG. 1, the analytic system is provided by Cloud Computing System 160 that provides storage and analysis of strike data, and may provide feedback to the athlete based on the analyzed data. Cloud computing system 160 may also comprise computing resources used to support interaction among athletes across target systems. For example, athletes may compete in a multi-player game or competition, and the cloud may receive data from each of the target systems in real time and evaluate and determine the state of the game accordingly. In an alternate embodiment, the analytic system may be provided by a system hosted by an entity providing the combat scoring system. The analytic system is not required to be hosted in a cloud. However, to host multi-user games and competitions, the analytic system may need to be accessible from geographically dispersed target systems.

User Access Point 165 provides a user interface to an athlete for establishing an account on the combat scoring system, configuring training session parameters, and initiating a personal training session. In an embodiment, the user access point may communicate over a wide-area network with the cloud processing and storage services to store and retrieve account and session data.

In an alternate embodiment, a single target system may be used for an athlete to train solo, without interacting with other athletes. In this case, the cloud computing system 160 need not to be used for interpreting multiple system data as described above. Thus, in an alternate embodiment the analysis, storage, and retrieval of session data provided by cloud computing system 160 may be implemented in a system local to an individual target system.

In another embodiment, the system shown in FIG. 1 may be used during an official competition, such as in the Olympics, to supplement or replace human judges in determining when and how many points should be awarded.

Target System

Figure 2:
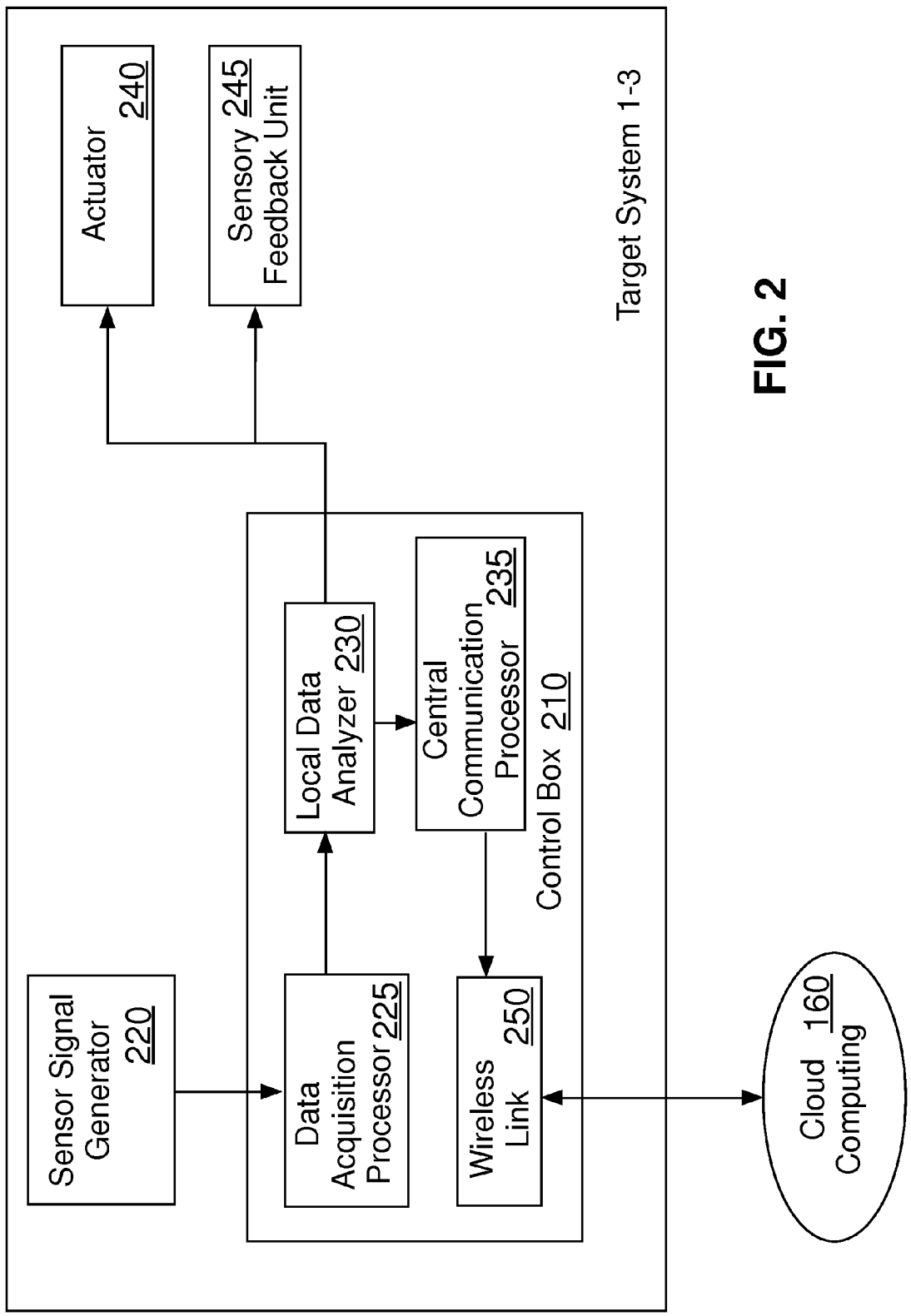
FIG. 2 is a block diagram of the components of a target system, according to an embodiment of the invention.

FIG. 2 is a block diagram of the components of a target system, according to an embodiment of the invention. The large rectangle represents a single target system, such as any of Target Systems 1-3. As shown in FIG. 1, each target system communicates with the cloud computing system 160. A target system may comprise one or more sensor signal generators 220 (also referred to as sensor systems), with each sensor system corresponding to a distinct target within the target system. Rather than embedding the sensor system in a garment worn by the athlete as described in prior patents, the sensor systems may be attached to a target. Each target may provide a specific location to strike for determining accuracy and/or a feedback mechanism for indicating a successful strike of that target. Each target may be distinctly configured to award points based on the accuracy, impact, timing, and direction of a strike on that target. For example, a mannequin of a human body may be instrumented as a target system with individual targets on various parts of the body. A strike to the head may result in a different amount of points awarded in Tae Kwon Do as compared to a strike on the torso. When the system is used for foil fencing, however, a strike to the head may not be awarded with any points.

A target system may also include a Control Box 210, an Actuator 240, and a Sensory Feedback Unit 245.

Sensor System

The sensor signal generator 220 comprises one or more sensor units. In an embodiment, a sensor unit may be a sensor matrix as disclosed in U.S. Pat. No. 7,891,231. A sensor matrix is a collection of one or more types of sensors that are interconnected spatially and logically to more accurately detect the impact and motion. For example, a sensor matrix may comprise gyroscopes, accelerometers, piezoelectric wires and magnetic field detection. A matrix of piezo electrical sensors and the magnetic field detection sensors may determine the magnitude of the impact as well as the location of the impact. When the source of the magnetic field is mounted to a foot or hand, the system may differentiate between the impact sources. The IMU is a matrix of 3 accelerometer and 3 angular rate sensors. When this matrix of sensors is embedded in a target, one can derive the impact and the direction of the source of impact by detecting and computing the resulting motion. On impact, the target experiences movement with velocity and the direction that is proportional to the magnitude of impact and the direction of the impact.

By combining the sensor information from the sensor matrix, the action or the environment of the action can be described more accurately. For example, a combination of a piezoelectric wires and the magnetic field can describe the magnitude of the impact as well as the source of the impact. A gyroscope and the accelerometer combination can detect motion in 3 dimensions as well as the magnitude of the force that caused the motion. The rate of change in angular position derived from the angular rate sensor can produce the angular acceleration of a target. By combining this information regarding the mass of the target, the force required to initiate this motion can be derived. A system that uses multiple sensors of the same type produces more accurate information of an action. For example, by averaging the output of a multiple piezoelectric sensors, and impact can be measured more accurately.

A sensor matrix may be embedded within a target, and the sensors may be activated when the sensors are directly hit. A successful target strike activates the sensors in the matrix, which generates one or more signals that are delivered into a control box 210.

Impact Sensors

The ideal impact sensor should be economical, rugged, and consume little or no power during normal operation. There are two types of sensors that meet these requirements: piezo cable and piezo sheet. FIGS. 6A-6C illustrate designs for a piezo sheet sensor, according to an embodiment of the invention. Both piezo cable and sheet sensors are constructed of polymers that convert mechanical energy into electrical signals. The mechanical energy changes the shapes and the inter-molecular relationship of polymers that makes up the piezo materials. These changes generate electrical charges that can be measured with proper interface hardware as described in the referenced patent. The piezo cables are inherently rugged, however, it can only sense in linear form. In order to sense two dimensional area with acceptable accuracy and consistency, it must be applied in a circular form or any other form that allows two dimensional coverage of the target. The sheet sensors are two dimensional, but the sensing materials are fragile. In order to prevent failure, the sheet sensors are laminated with material that provides protection.

In either case, the magnitude of mechanical deformation due to the impact generates corresponding magnitude in electrical charge. The relation is:

$Q=K \times Force$: Charge generated=constant conversion factor×Force applied

Using the Ohm's law, voltage=current×Resistance, the following relationship is established $V=I \times R=dQ/dt \times$ Impedance, $dQ/dT=$instantaneous change in charge*the resistivity characteristic of the material. Substituting the Q, $V=(d(K \times Force)/dt) \times$ impedance: the relationship between Force and voltage.

The constant conversion factor is typical property of the material which is specified by the manufacturers.

IMU

A distinctive feature of this combat scoring system is that an inertial measurement unit (IMU) may be used to implement sensor signal generator 220. An IMU comprises an ultra-low cost inertial measurement sensor, which when mounted on the target system, can detect the roll and pitch of target movement after an impact. The vector position displacement and the rate of the displacement can be used to estimate the direction and the magnitude of the impact. In an embodiment, the additional magnetometers used in avionics may not be needed for detecting yaw. In the target motion detection, a set of 3 axis accelerometer and 3 axis angular motion sensors may be adequate. An additional piezo sensor may be used in parallel to measure instantaneous impact while an IM sensor may measure the motion due to the impact. As a result, an IMU-based sensor system may be mounted onto a target device such as on top of a punching bag or some other place outside of the strike zone, because the IMU-based sensor system need not be struck directly. The punching bag is struck and that energy and motion is transferred to the sensor system 220 where the impact data may be analyzed and recorded. In an embodiment in which only an IMU is used in a target system, instrumented targets are not required to derive strike force and angle. The force and direction of the strike can be determined by just the IMU when the weight of the target is known, such as when the IMU system is mounted onto a heavy punching bag. In this embodiment, the athlete may strike the punching bag, and the system may record impact magnitude and direction of the athlete's strikes.

As mentioned earlier, the control box 210 receives signals from the sensor system 220. In an embodiment, the signals may be analog or digital signals. The control box 210 may interpret the received signals, and sends a message over a network to store the data and for potentially additional analysis. In an embodiment, the control box 210 may comprise components including a Data Acquisition Processor 225, a Local Data Analyzer 230, a Central Communication Processor 235, and a Wireless Link 250.

The data acquisition processor 225 receives signals from one or more sensor systems 220. For example, one or more Hall sensors may provide a signal to indicate that the sensor was hit. Proximity to a target location may be determined by receiving signals from a variety of Hall sensor types. For example, a commercially available point Hall sensor may indicate a point location of the hit (i.e. the bull's eye) because only a hit very near the location of the sensor generates a signal. Other Hall sensors may be custom built to cover a wider area around the target and generate a signal to register a hit farther away from the sensor. By comparing the signals generated by the various Hall sensors, the distance of the hit from the target point may be determined. In an embodiment of the invention, dedicated proximity sensors may not be used. Signals received from other sensors that are placed at known locations may be used to determine the location of the hit.

A sensor system 220 comprising one or more accelerometers may provide a measurement of acceleration (i.e. Velocity/time which may be expressed as m/sec$^2$ or expressed in g-force units (g's) 1 g=9.8 m/sec$^2$. An angular rate sensor in the sensor system 220 may provide data on the angle of the impact per time, and the data may be expressed in degrees/sec or radians/sec. There may be an angular rate sensor associated with each dimension of 3-dimensional space. Thus, one angular rate sensor may report on angular displacement in the yaw axis (measuring yaw), a second angular rate sensor may provide data on angular displacement in the pitch axis (measuring pitch), and the third angular rate sensor may provide data on angular displacement in the roll axis (measuring roll).

The data acquisition processor 225 may also associate a timestamp with received data that is determined to represent an impact. The timestamp may be used to determine the elapsed time between when a target flashes and when associated impact data is received for that target (i.e. response time). If the received signals are analog signals, the data acquisition processor 225 may convert the signals to digital data. The data acquisition processor 225 may further determine the force and the energy of the impact based on the sensor signals received. For example, force may be determined by:

force=mass*acceleration.

The mass of the target may be pre-configured into the system, and the acceleration is provided by input from accelerometers as described above. Thus, the force of an impact may be computed based on the pre-configured mass of the target and the received acceleration data. Energy, which may be measured in Joules, may be determined by:

energy=force*displacement

Energy may be computed by further multiplying the force of the impact with the displacement of the target which is received from angular rate sensors as described above.

The local data analyzer 230 may receive the digital data provided by the data acquisition processor 225 and interpret the data. For example, the local data analyzer 230 interprets the sensor data according to the configuration parameters established for the session. For example, the local data analyzer 230 may compare the amount of force/energy and displacement of the strike against one or more configured thresholds to determine whether a valid hit was made and to determine how many points to assign such a hit.

If a valid strike is determined, the interpreted data may be sent to the central communication processor 235 that packages the data and controls transmission with required security of the data over a network for storage and processing such as provided by cloud computing system 160. In an embodiment, the network between the control box 210 and the analytic system 400 (FIG. 4) is a wireless link 250. For example, wireless link 250 may transmit data to the cloud computing system 160 over a wireless LAN (WiFi) to an Internet access point. In an embodiment in which the storage and processing system is co-resident with the target system, a LAN-based network or peer-to-peer connection may be used.

In an embodiment, the control box 210 may be installed/mounted on the target system away from the strike zone.

The target system may optionally include an Actuator 240 and/or a Sensory Feedback Unit 245 for responding to a detected strike in real-time. The sensory feedback unit 245 may provide any kind of sensory feedback such as visual or auditory feedback for informing the athlete of a valid strike and/or the quality of a strike. For example, the sensor feedback unit may comprise one or more lights that illuminate to indicate the validity and quality of a strike. Whereas a single light may indicate a successful strike on a particular target, the illumination of multiple lights may indicate the quality of the strike. Alternatively, one or more seven-segment LED, VFD, or LCD displays that illuminate a numeral (such as in a digital clock) may be used to display a number proportional to the quality (e.g. score). Auditory feedback that can vary in volume, pitch, and rhythm may be used to signal success and score of a strike. For example, a higher pitch tone may indicate a higher score. A strike that is not valid may result in a low pitch tone. Another example may be that crowd cheering noise may be played for a valid strike and a louder volume may indicate the quality of the strike. This may be beneficial for conditioning an athlete to adjust to concentrating in a competition with live spectators.

Although not shown in FIG. 2, a target system may also provide the ability for a user to authenticate to the target system and/or to configure options for interacting with the target system. In such an embodiment, the athlete may use the target system without using the user access point to initiate each session. Such a feature may be advantageous if the athlete is unable to obtain a network connection within the training facility premises. The target system user interface components may comprise buttons or other touch sensitive areas, switches, voice recognition, short range wireless connection techniques such as low energy Bluetooth, near-field sensing, or RFID, etc. Lights, LCD display, and/or speech synthesis, may provide prompts and or feedback regarding the status of authentication and/or configuration.

An actuator 240 may be used to respond to a strike with physical movement of an object. This component may be useful for constructing an automated, robotic, sparring partner with the ability to react to an athlete's strike.

Depending on the location of the control box 210, the actuator and/or sensory feedback unit may be mounted on the target system outside of the control box 210 or installed inside the control box 210. For example, if the control box 210 is mounted on the target system within line of sight and/or hearing of the athlete, the sensory feedback unit 245 may be installed on or in the control box 210. If the control box 210 is installed out of sight or hearing from the athlete, then the sensory feedback unit may be a unit installed separately from the control box 210. Similarly, if an actuator is used to control a robot that is instrumented as a target system, actuator 240 may be placed inside the control box or separately from the control box 210.

Configuration and Display of Session Data

To use the system, a user may choose to go through two steps: 1) authenticate (i.e. "log-in") and then 2) configure their workout session. If the user is also the owner of the system, authentication may not be necessary since the system may already be registered to the owner (the administrator) and it will send all session data to the owner's or administrator's user account. The system may allow anonymous users to train and play games, with fewer options for storing and reporting the session data. In this embodiment, authentication may not be necessary, and all session data may be sent to the default user or system administrator account.

Authentication may be accomplished by several methods. The user may use various techniques to identify him or herself so that the session data is recorded in his or her user account in the analytic system. Authentication options may include bio-metric identification (such as, but not limited to, voice, fingerprint recognition, or retinal scan) or use of a wireless fob 405 (FIG. 4) that employs a simple code to communicate with the control box 210. When activated, the fob 405 may send a unique code to the control box 210, and the control box 210 may send the code to the analytic system 400 (FIG. 4) to authenticate and allow the session data to be logged to the user's account. Alternatively, authentication may be achieved by using the targets on the system as buttons on a keypad, and entering a unique identifier code.

Once the athlete chooses to authenticate or use the system anonymously, the athlete may choose to either train with a default session configuration, train with the most recent session configuration, a randomly chosen configuration, or set up a new configuration. Sessions may be configured by several methods such as through the user access point 165 (e.g., via a web browser or handheld device), by communicating with the control box 210 with voice recognition or motion gesture techniques, or by using the targets as buttons on a keypad. In an embodiment, the athlete may activate a session configuration through the targets or the control box 210, and then set parameters in a sequence with the targets—Target #1 may be pressed to set the target sequence program (either random, by numeric sequence, or reverse numeric sequence, for instance); Target #2 may then be pressed to set the time-out interval, and then Target #1 may be pressed to set the session to run in 1 minute rounds; Target #3 may then be pressed to set the number of "rounds" in the session, the athlete may then touch Target #6 to indicate that they want to train with 6 rounds each lasting 1 minute; Target #4 may then be pressed to set the time-out duration (the maximum time that a target will be lit before the session moves on to the next target. The user must strike the target within this time limit to score). Other targets or combinations of targets may be used to configure the system in other ways, such as multi-player game sessions, or skill levels.

At the end of the session, data collected during the session may be displayed locally on a display device local to the target system, without requiring access to a user access point.

In an embodiment, an athlete may use a user access point user interface to interact with an application to configure one or more sessions and to view data previously collected during a training session. An application accessible through the user access point 165 may provide an account management user interface, a session management user interface, and a data analysis and display interface. A session refers to a period of time during which training, gaming, or competition takes place. The system components may be activated and/or configured at the beginning of a session and deactivated and powered down at the end of a session.

Before the first training session or other use of the target system, an account may be created for the athlete in the combat scoring system. The athlete may log into the account and configure parameters for one or more sessions. Session parameters may include a specification of the number of rounds and a specification of when a round ends (e.g. elapsed duration of the rounds, total number of rounds or strikes, total number of valid strikes, reaching a specified cumulative point score, etc.) or a specification of the duration of the session as a whole. One or more target systems may be associated with a user account once the account is configured. Configuring a session may include selecting one of the target systems associated with the athlete's account for use during the session. For purposes of explanation, the example herein assumes a single target system is used in a session. Other session parameters may include the kind of training or game challenges to be represented. For example, if the athlete requests to measure response time, the system may generate a "go" signal on an individual target among several targets. A session may also be configured to interact with another athlete using a different target system. In addition, target system thresholds may be configured to determine how much force is required to validate a strike, a direction from which a valid strike must come, the maximum amount of time after a "go" signal is issued during which a strike will register, etc. Choices for these parameters may reflect the skill level of the athlete, the height/weight of the athlete, and the rules of the sport. Configuring these various parameters will result in very different experiences from a personal training workout, individual game, or multi-player game.

Figure 3:
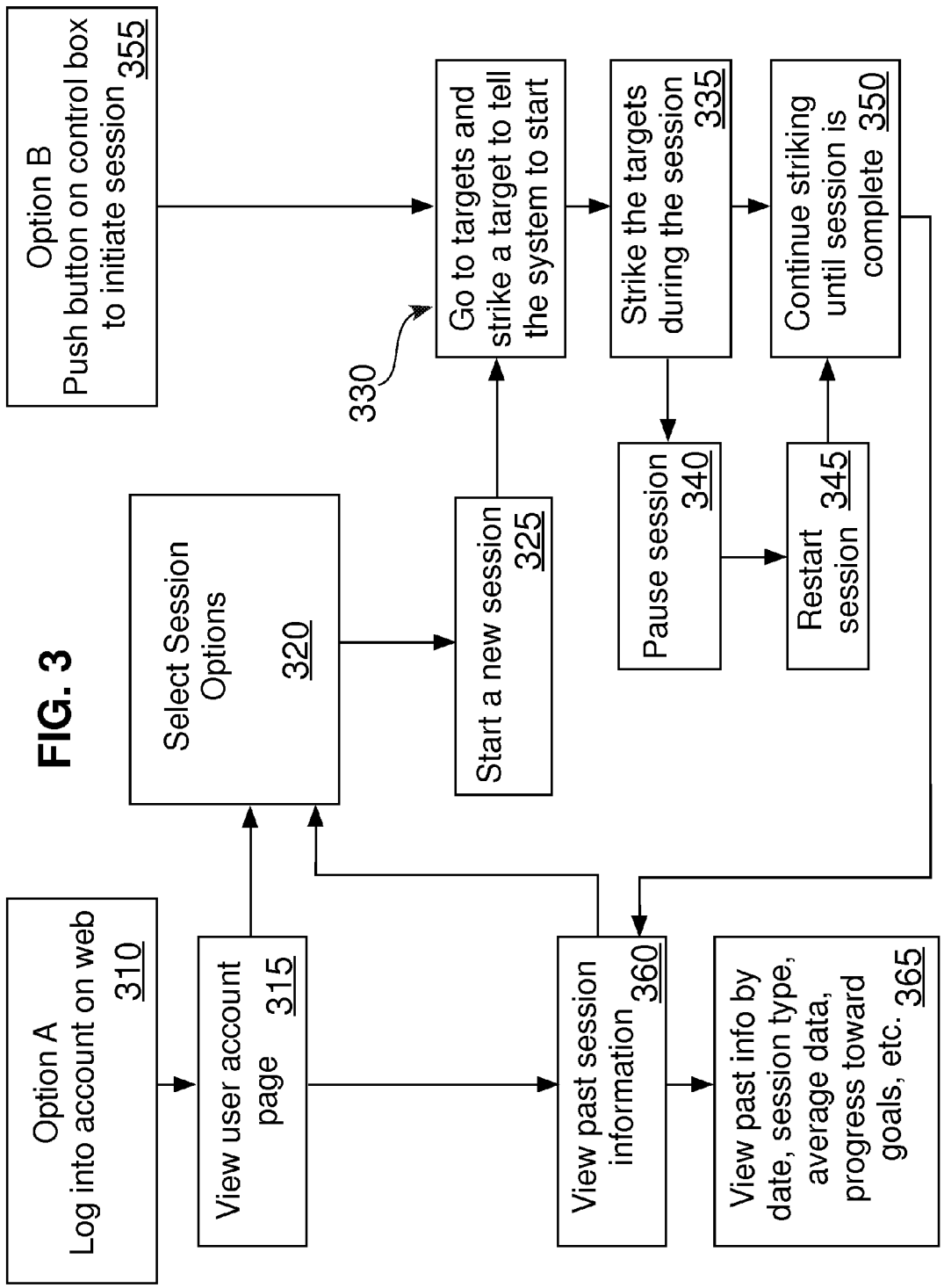
FIG. 3 is a high level flow diagram showing the steps for using a combat scoring system, according to an embodiment of the invention.

FIG. 3 is a high level flow diagram showing the steps for initializing and using the combat scoring system, using the user access point 165, or using the user interface provided by a target system. The flow starting with Option A describes interacting with the system through the user access point 165. At Step 310, an athlete may log into their personal training account over the network. In an embodiment, the network may be the Internet. Alternatively, if the analytic system 400 resides co-located with the target system, the network may be a local area network (LAN). Upon logging in, the athlete may be shown their user account page in Step 315. From the user account page, the athlete may choose to start a new training session or to view the data from past sessions as in Step 360. For viewing past data session information, charts, graphs, and raw data may be displayed by date, session types, averages, progress toward a goals, etc. in Step 365.

From the user account page or view past session information page, a new session may be initiated in Step 320. In an embodiment, previously configured sessions may be named, and the collection of parameters previously configured may be selected by name or other identifying information to be used for configuring the session about to start. Alternatively, a new configuration may be created for the new session. Once configured, the new session may be started at 325, and the analytic system 400 prepares to receive, analyze, and store data for this session.

The flow starting with Step 355 labeled "Option B" describes an athlete interacting with user interface devices in or around the target system itself. For example, a default session type may be started by pushing a button on the control box 210 of a target system or striking a sensor in a particular target may serve to enter configuration data. In an embodiment, the control box 210 or other device associated with the target system may accept input used for athlete authentication such as biometric data (finger print, retinal scan, voice recognition) or read a Radio Frequency Identification (RFID) tag such as a card key. Other wireless technologies such as low-energy Bluetooth or Near Field Communication (NFC) may alternatively be used to communicate authentication information from a wireless fob 405 (FIG. 4) to a receiver in the target system. Authenticating the user may be important to ensure that the data for the session is stored in association with the correct user's account.

Once the session is initiated in Step 325, the analytic system is ready to receive session data, and the one or more target systems to be used in the session are activated in Step 330. In an embodiment, when initiating a session via a target system control box, Step 330 may be included in Step 355. To activate a target system, one or more targets within the system may be struck, or the athlete may push a button, flip a switch, or provide other user input to user input facilities provided by the target system.

In Step 335, the athlete strikes one or more targets during the session and data is collected and sent to the analytic system 400 as described above. A session may be paused in Step 340, and restarted in Step 345. When the end of the session is detected based on the configuration, the session ends in Step 350.

Analytic System

Figure 4:
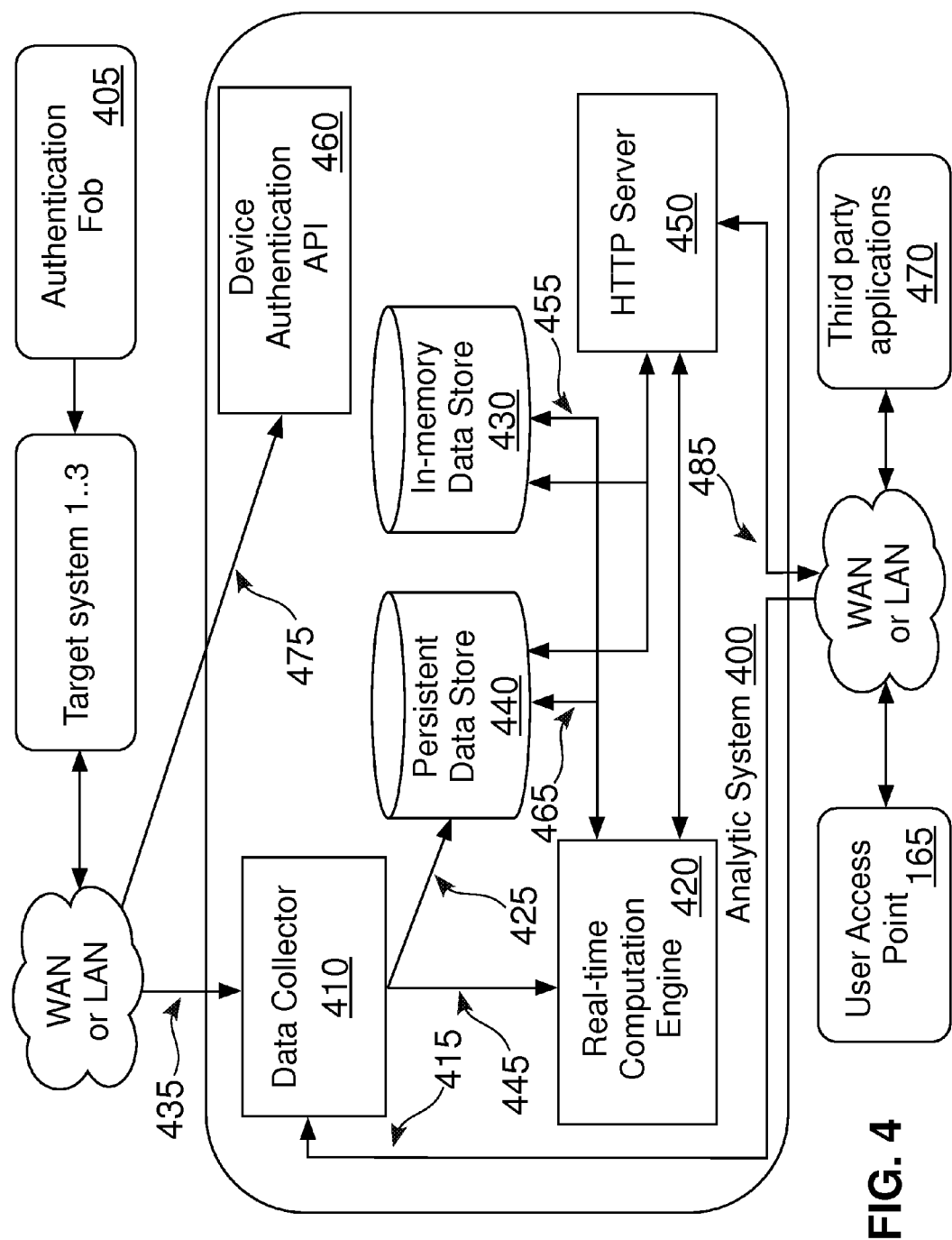
FIG. 4 is a high level data flow diagram showing the flow of data among components within the analytic system, according to an embodiment of the invention.

The analytic system 400 is a storage and processing system where data from target systems may be processed and stored, and which holds user account information. FIG. 4 is a high level data flow diagram showing the flow of data among components within the analytic system 400, according to an embodiment of the invention. Analytic System 400 comprises components including Data Collector 410, Device Authentication API 460, Real-time Computation Engine 420, In-Memory Data Store 430. Persistent Data Store 440, and HTTP (web) Server 450.

Data flow 415 represents the data that flows between the user access point 165 that may reside across a network from analytic system 400 and the data collector 410 within analytic system 400. Data flow 415 may include user registration data, authentication information for account login, and specification of session options. Data flow 425 represents the flow of data between the data collector 410 and the persistent data store 440. User registration data, authentication, session configuration data is stored in the data store, and retrieved for authentication or update purposes. Data flow 485 represents analyzed and/or aggregated data retrieved from the data store and displayed at the user access point 165.

Data flow 435 represents the flow of session data from one of the target systems to analytic system 400. The data collector 410 receives the data and forwards the data through flow 445 to the real-time computation engine 420. The data is processed and sent to the In-memory store 430 via flow 455 and then to the user access point 165 for display. Additionally, the data may be sent through flow 465 to the persistent data store 440 for long-term storage and retrieval. Data flow 475 represents data from a user authentication device, such as from Authentication Fob 405, sending user and target system information to the device authentication API 460.

The analytic system 400 may provide a set of API's that Third Party Applications 470 may use to store and retrieve data to/from the analytic system. Facebook or other social media applications are examples of such third party applications.

An Example Machine Overview

Figure 5:
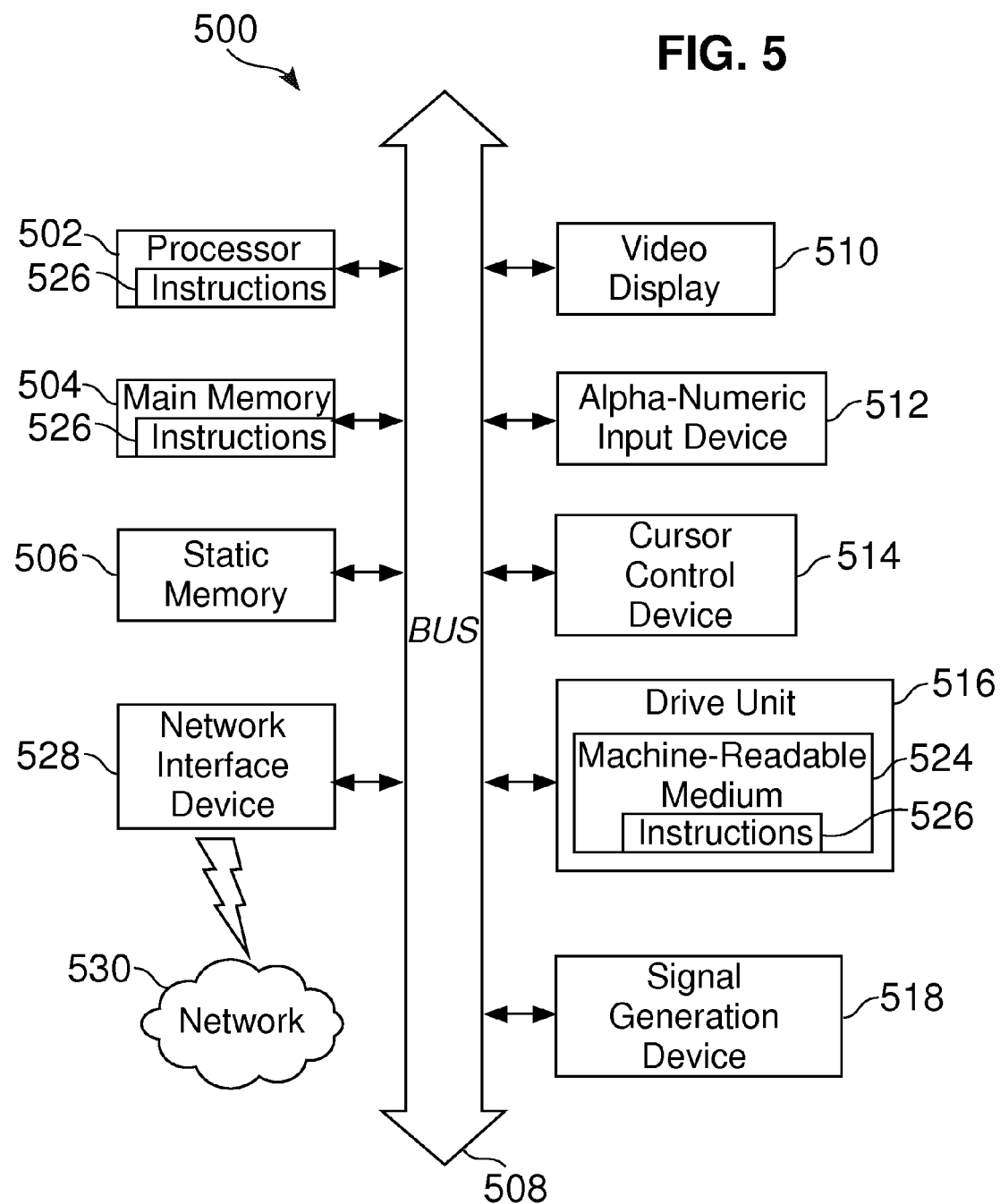
FIG. 5 is a block schematic diagram of a machine in the exemplary form of a computer system, according to an embodiment of the invention.

FIG. 5 is a block schematic diagram of a machine in the exemplary form of a computer system 500 within which a set of instructions may be programmed to cause the machine to execute the logic steps of the invention. In alternative embodiments, the machine may comprise a network router, a network switch, a network bridge, personal digital assistant (PDA), a cellular telephone, a Web appliance or any machine capable of executing a sequence of instructions that specify actions to be taken by that machine.

The computer system 500 includes a processor 502, a main memory 504 and a static memory 506, which communicate with each other via a bus 508. The computer system 500 may further include a display unit 510, for example, a liquid crystal display (LCD) or a cathode ray tube (CRT). The computer system 500 also includes an alphanumeric input device 512, for example, a keyboard; a cursor control device 514, for example, a mouse; a disk drive unit 516, a signal generation device 518, for example, a speaker, and a network interface device 528.

The disk drive unit 516 includes a machine-readable medium 524 on which is stored a set of executable instructions, i.e. software, 526 embodying any one, or all, of the methodologies described herein below. The software 526 is also shown to reside, completely or at least partially, within the main memory 504 and/or within the processor 502. The software 526 may further be transmitted or received over a network 530 by means of a network interface device 528.

In contrast to the system 500 discussed above, a different embodiment uses logic circuitry instead of computer-executed instructions to implement processing entities. Depending upon the particular requirements of the application in the areas of speed, expense, tooling costs, and the like, this logic may be implemented by constructing an application-specific integrated circuit (ASIC) having thousands of tiny integrated transistors. Such an ASIC may be implemented with CMOS (complimentary metal oxide semiconductor), TTL (transistor-transistor logic), VLSI (very large systems integration), or another suitable construction. Other alternatives include a digital signal processing chip (DSP), discrete circuitry (such as resistors, capacitors, diodes, inductors, and transistors), field programmable gate array (FPGA), programmable logic array (PLA), programmable logic device (PLD), and the like.

It is to be understood that embodiments may be used as or to support software programs or software modules executed upon some form of processing core (such as the CPU of a computer) or otherwise implemented or realized upon or within a machine or computer readable medium. A machine-readable medium includes any mechanism for storing or transmitting information in a form readable by a machine, e.g. a computer. For example, a machine readable medium includes read-only memory (ROM); random access memory (RAM); magnetic disk storage media; optical storage media; flash memory devices; electrical, optical, acoustical or other form of propagated signals, for example, carrier waves, infrared signals, digital signals, etc.; or any other type of media suitable for storing or transmitting information.

Other Embodiments

In addition to embodiments used for competition, training, or gaming, another embodiment may be used for spectator entertainment. For example, data generated by the system may be superimposed on a monitor screen in view of spectators at a live event or on a television or computer screen during a broadcast or telecast boxing match. The system may be augmented to allow viewers of the broadcast/telecast to guess as to future data points (e.g. how hard will competitor A hit his opponent next time, or how many blows will competitor B land on his opponent in the $5^{th}$ round that reach a certain threshold of force, or what will be the average force of blows delivered by Competitor A over the course of the entire match. Such an embodiment may be used in Las Vegas or other places with legalized gambling on contact sports.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

Furthermore, although elements of the invention may be described or claimed in the singular, reference to an element in the singular is not intended to mean "one and only one" unless explicitly so stated, but shall mean "one or more". Additionally, ordinarily skilled artisans will recognize that operational sequences must be set forth in some specific order for the purpose of explanation and claiming, but the present invention contemplates various changes beyond such specific order.

The invention claimed is:

1. A combat scoring system, comprising:
   a user access point;
   an analytic system;
   one or more target systems, wherein each of the target systems includes
      a plurality of impact targets, wherein each of the impact targets is associated with a specific location to strike, wherein each of the impact targets includes a sensor matrix embedded within that includes a plurality of sensor systems that are interconnected spatially and logically with respect to each other for a corresponding impact target, to generate one or more sensor signals when struck for detection of impact and motion with respect to a specific sensor system of the plurality of sensor systems of the sensor matrix of the corresponding impact target; and
      a control box, including a processor, wherein the control box is linked to the analytic system;
   wherein the analytic system is enabled to:
      establish a user account that corresponds to an athlete, through interaction by a user through the user access point,
      allow the athlete to access the corresponding user account through interaction with a selected target system, and
      allow the athlete to initiate a session at the selected target system through the accessed corresponding user account;
   wherein during the initiated session, the processor is enabled to provide feedback to the athlete corresponding to interaction between the athlete and one or more of the impact targets, wherein for each of the corresponding impact targets, the feedback includes impact information and accuracy information corresponding to the interaction between the athlete and the specific sensor system of the plurality of sensor systems of the sensor matrix of the corresponding impact target; and
   wherein, responsive to interaction between the athlete and one or more of the impact targets during the initiated session, impact data responsive to the session is acquired and stored at any of the control box or the analytic system, wherein the acquired and stored impact data is associated with the user account for the athlete, and wherein the acquired and stored impact data can be retrieved by any of the athlete and the user.

2. The combat scoring system of claim 1, further comprising:
   a sensory feedback unit for indicating a successful strike of one or more of the impact targets, wherein the sensory feedback unit provides feedback as an auditory signal or a visual signal.

3. The combat scoring system of claim 1, wherein each impact target is configured to detect a valid strike based on any of accuracy, impact force, timing, and direction of a strike.

4. The combat scoring system of claim 1, further comprising:
   an inertial measurement unit (IMU) mounted on the combat scoring system, wherein the IMU includes one or more accelerometers and one or more gyroscopes, the IMU configured to measure the impact data based on movement of one or more of the impact targets as a result of a strike.

5. The combat scoring system of claim 1, wherein each of the sensor matrices includes any of:
   a plurality of sensors for measuring instantaneous force of a strike's impact; or
   a plurality of sensors for determining accuracy of a strike relative to the associated impact target.

6. The combat scoring system of claim 1, wherein the one or more target systems include a plurality of target systems;
   wherein the impact data from each of the plurality of target systems is stored to and retrieved from a common storage system; and
   the impact data from each of the plurality of target systems is accessible from the common storage system over a wide-area network.

7. The combat scoring system of claim 1, wherein each of the target systems is enabled to communicate the impact data to and from the analytic system over a wireless link.

8. The combat scoring system of claim 1, wherein proximity of a strike relative to a particular impact target is determined by a plurality of location sensors for each of the sensor matrices.

9. The combat scoring system of claim 1, wherein the processor is configured to determine a force value and an energy value associated with the signals received in response to an impact target strike.

10. The combat scoring system of claim 1, wherein the analytic system is remotely located in a cloud computing system; and
   wherein the processor, responsive to determining that a particular strike is a valid strike, sends the impact data to the cloud computing system over a wide area network, wherein the impact data is stored at the analytic system and is associated with the user account associated with the athlete;
   wherein the cloud computing system is available to one or more other athletes, to participate in the same session or a different session.

11. The combat scoring system of claim 1, further comprising:
a sensory feedback unit for prompting the athlete to strike a particular impact target;
wherein the processor is enabled to determine a response time between a time of prompting and a time a strike is detected on the particular impact target.

12. The combat scoring system of claim 1, further comprising:
an actuator that is configured to cause a portion of a corresponding target system to move in reaction to a strike of a selected impact target by the athlete.

13. The combat scoring system of claim 1, wherein the analytic system is local to one of the target systems.

14. The combat scoring system of claim 1, wherein the analytic system is remote from each of the target systems.

15. The combat scoring system of claim 1, wherein the control box is linked to the analytic system over an internet connection.

16. The combat scoring system of claim 1, wherein the athlete can participate in the session against at least one other athlete.

17. The combat scoring system of claim 16, wherein the athlete can participate in the same session against the at least one other athlete in real time.

18. The combat scoring system of claim 16, wherein the at least one other athlete is located at the target system associated with the athlete.

19. The combat scoring system of claim 16, wherein the at least one other athlete is located at one of the target systems other than the target system associated with the athlete.

20. A combat scoring method, comprising:
establishing a user account at an analytic system, through interaction by a user at a user access point that is remote from the analytic system, wherein the user account corresponds to an athlete;
allowing the athlete to access the corresponding user account through interaction with a selected target system of one or more target systems, wherein each of the target systems includes
a plurality of impact targets, wherein each of the impact targets is associated with a specific location to strike, wherein each of the impact targets includes a sensor matrix embedded within that includes a plurality of sensor systems that are interconnected spatially and logically with respect to each other for a corresponding impact target, to generate one or more sensor signals when struck for detection of impact and motion with respect to a specific sensor system of the plurality of sensor systems of the sensor matrix of the corresponding impact target; and
a control box, including a processor, wherein the control box is linked to the analytic system;
initiating a session for the athlete through the accessed user account at the selected target system;
with the processor,
acquiring impact data responsive to interaction between the athlete and one or more of the impact targets during the initiated session,
providing feedback to the athlete during the initiated session, wherein the feedback corresponds to interaction between the athlete and one or more of the impact targets, wherein for each of the corresponding impact targets, the feedback includes impact information and accuracy information corresponding to the interaction between the athlete and the specific sensor system of the plurality of sensor systems of the sensor matrix of the corresponding impact target; and
storing the acquired impact data at any of the control box or the analytic system, wherein the stored impact data is associated with the user account for the athlete; and
retrieving the stored impact data associated with the user account for the athlete by any of the athlete and the user.

21. The method of claim 20, further comprising:
upon the initiating the session at the selected target system, receiving a configuration parameter from the athlete for the session.

22. The method of claim 21, wherein the configuration parameter includes any of a default session configuration, a recent session configuration, and a new configuration.

23. The method of claim 21, wherein the configuration parameter is received from the athlete through any of the user access point, the control box, through voice recognition, through motion gesture techniques, or by using the impact targets as buttons on a keypad.

24. The method of claim 20, wherein the athlete participates in the session against at least one other athlete.

25. The method of claim 24, wherein the athlete participates in the same session against the at least one other athlete in real time.

26. The method of claim 24, wherein the at least one other athlete is located at the target system associated with the athlete.

27. The method of claim 24, wherein the at least one other athlete is located at one of the target systems other than the target system associated with the athlete.

28. The method of claim 20, wherein the user is associated with the athlete, wherein the user is any of a coach, a parent, a judge, or an athlete other than the athlete.

29. The method of claim 20, further comprising:
upon the initiating the session at the selected target system, receiving an option specified by the athlete for the session.

30. The method of claim 20, wherein the option specified by the athlete for the session includes any of a number of training rounds, a length of the training round measured by any of time or a number of impacts, an interval and pattern of impact challenges, and for playing various games against other players either locally or over a network.

31. The method of claim 20, wherein the sensors for each of the sensor systems include at least one sensor of each of a plurality of sensor types that are configured for different types of measured parameters.

32. The combat scoring system of claim 1, wherein the sensors for each of the sensor systems include at least one sensor of each of a plurality of sensor types that are configured for different types of measured parameters.

* * * * *